United States Patent
Buchholz et al.

(10) Patent No.: US 10,203,302 B2
(45) Date of Patent: Feb. 12, 2019

(54) STATE OF HEALTH MONITORING AND RESTORATION OF ELECTROCHEMICAL SENSOR

(71) Applicant: Carrier Corporation, Jupiter, FL (US)

(72) Inventors: Matthew J. Buchholz, Canon City, CO (US); Lei Chen, South Windsor, CT (US); Zhiwei Yang, South Windsor, CT (US); Valeriy V. Miagkov, Colorado Springs, CO (US)

(73) Assignee: CARRIER CORPORATION, Farmington, CT (US)

( * ) Notice: Subject to any disclaimer, the term of this patent is extended or adjusted under 35 U.S.C. 154(b) by 288 days.

(21) Appl. No.: 15/226,256

(22) Filed: Aug. 2, 2016

(65) Prior Publication Data

US 2017/0045474 A1 Feb. 16, 2017

Related U.S. Application Data

(60) Provisional application No. 62/204,618, filed on Aug. 13, 2015.

(51) Int. Cl.
  *G01N 27/327* (2006.01)
  *G01N 27/416* (2006.01)
  *G01N 27/61* (2006.01)
  *G01N 27/407* (2006.01)

(52) U.S. Cl.
  CPC ............... *G01N 27/4163* (2013.01)

(58) Field of Classification Search
  CPC .. G01N 27/10; G01N 27/4163; G01N 27/304; G01N 27/3274; G01N 27/407; G01N 27/4175; G01N 27/61
  See application file for complete search history.

(56) References Cited

U.S. PATENT DOCUMENTS

| 4,532,013 A | 7/1985 | Dietz et al. |
| 4,772,375 A | 9/1988 | Wullschleger et al. |
| 4,819,602 A | 4/1989 | Mieno et al. |
| 4,897,162 A | 1/1990 | Lewandowski et al. |
| 4,938,194 A | 7/1990 | Kato et al. |
| 5,916,156 A | 6/1999 | Hildenbrand et al. |
| 5,958,214 A | 9/1999 | Nikolskaja |

(Continued)

FOREIGN PATENT DOCUMENTS

| GB | 2194056 A | 2/1988 |
| WO | 2008058832 A1 | 5/2008 |

*Primary Examiner* — Susan D Leong
(74) *Attorney, Agent, or Firm* — Cantor Colburn LLP (57) ABSTRACT

A method of manufacturing an electrochemical sensing system is provided. The method includes forming a sensor with a first sensing element disposed on a sensor, the first sensing element configured to detect a target gas, disposing a second sensing element on the sensor, the second sensing element configured to detect the target gas, and coupling a protective feature to the second sensing element, the protective feature configured to prevent non-target gases from contacting the second sensing element. The sensor is configured such that if the first sensing element generates a current exceeding a first threshold current value and the second sensing element does not exceed a second threshold current value it is determined that the first sensing element is contaminated and a restoration protocol is performed on the first sensing element.

19 Claims, 4 Drawing Sheets

(56) References Cited

U.S. PATENT DOCUMENTS

| | | | |
|---|---|---|---|
| 5,985,673 A | 11/1999 | Bao et al. | |
| 6,007,697 A | 12/1999 | Yagi et al. | |
| 6,060,025 A | 5/2000 | Pasquariello | |
| 6,200,443 B1 | 3/2001 | Shen et al. | |
| 6,428,684 B1 | 8/2002 | Warburton | |
| 6,551,499 B1 | 4/2003 | Springhorn et al. | |
| 7,033,482 B2 | 4/2006 | Inoue | |
| 7,811,433 B2 | 10/2010 | Manoukian et al. | |
| 7,909,981 B2 | 3/2011 | Dalmia | |
| 7,938,944 B2 | 5/2011 | Suzuki | |
| 8,097,135 B2 | 1/2012 | Bakker et al. | |
| 8,317,998 B2 | 11/2012 | Pratt et al. | |
| 8,414,860 B2 | 4/2013 | Stancovski | |
| 8,840,775 B2 | 9/2014 | Chen et al. | |
| 2004/0238378 A1 | 12/2004 | Kumazawa et al. | |
| 2005/0100478 A1 | 5/2005 | Harvey | |
| 2005/0235735 A1* | 10/2005 | Doll | G01N 27/123 73/31.06 |
| 2008/0121946 A1* | 5/2008 | Youn | G01N 27/122 257/253 |
| 2010/0288652 A1 | 11/2010 | Pratt et al. | |
| 2013/0015064 A1 | 1/2013 | Masel et al. | |
| 2013/0087457 A1 | 4/2013 | Pratt et al. | |
| 2014/0033794 A1 | 2/2014 | Reinhardt et al. | |
| 2014/0311221 A1* | 10/2014 | Gole | G01N 27/127 73/31.06 |

\* cited by examiner

| Sensing Element | Sensing Element Configuration | First Target Gas | Contamination Gas | Second Target Gas | Third Target Gas |
|---|---|---|---|---|---|
| 1 | Unbiased sensing element, no protective feature | Y | Y | N | N |
| 2 | Unbiased sensing element, w/ protective feature | Y | N | N | N |
| 3 | Biased sensing element, no protective feature | Y | Y | Y | Y |
| 4 | Biased sensing element, w/ protective feature | Y | N | N | Y |

STATE OF HEALTH MONITORING AND RESTORATION OF ELECTROCHEMICAL SENSOR

CROSS-REFERENCE TO RELATED APPLICATIONS

The present application claims priority from U.S. Provisional Patent Application No. 62/204,618 filed Aug. 13, 2015. The contents of the priority application are hereby incorporated by reference in their entirety.

BACKGROUND

The subject matter disclosed herein generally relates to electrochemical sensors and, more particularly, to state of health monitoring and restoration of electrochemical sensors.

Electrochemical gas sensors are gas detectors that measure a concentration of a target gas by oxidizing or reducing the target gas at an electrode and measuring the current that is generated. Electrochemical gas sensors are normally designed to operate in a diffusion limited mode. This is normally achieved by using a capillary or membrane, which limits gas access in a well-defined and repeatable way. The sensor is designed such that the capillary or membrane provides the limiting factor. For example, the gas sensing electrode is designed to have sufficient activity reserve that the actual activity of the electrode can generally be ignored (since it is much greater than required to consume the available gas). Under certain conditions, however, sensors can deviate from the ideal diffusion limited behavior: for example, if the catalytic activity of the electrode degrades significantly, or if blocking or flooding occurs, then the sensor response may deviate from the predetermined relationship between concentrations of species to be detected and an analog output.

In addition to such faults which can result in a change in the level of gas response, certain faults can result in a reduction in the speed of response, even though the steady state response remains unchanged: for example, if the membrane electrode assembly becomes partially flooded or poisoned this may result in a slow response, and in some cases a reduction in steady state response. The same is true if the catalytic activity of the electrode is reduced, which can be a particular problem for sensors with low activity reserve.

An example of a gas that may be monitored, and related sensors which may be subject to faults, is low global warming potential (LGWP) refrigerants that may be used in HVAC systems. Various LGWP refrigerants are mildly flammable, and thus leak detection is desired. Electrochemical sensors have been successfully applied for toxic gas sensing. Passive fault mitigation methods such as adsorption by activated carbon have been used successfully to protect CO sensors from poisoning, i.e., electrode poisoning or saturation or coverage by an undesirable chemical. Such a method can be ineffective when the targeted species adsorbs on the adsorbent, resulting in substantial interference of the sensing process or completely defeat the detectability of the sensor. The electrochemical sensor failure mechanisms resulting from catalyst deactivation due to ambient volatile species can be extremely difficult to detect by the sensors, particularly when the sensors are deployed for leak detection expected to occur rarely. This is because during catalyst deactivation a sensor can generate a similar response as if a leak is detected and low cost electrochemical sensors may lack the ability to determine the identification of the species detected. However, it would be necessary to deploy a fail-safe operation of the sensors for safety monitoring, e.g., for leak detection of flammable refrigerants. Therefore, it is may be desirable to enable an electrochemical sensor to examine the state of health of the sensor pertaining to catalyst activity and restore the sensor's activity when the state of health is compromised due to exposure to active species.

SUMMARY

According to one embodiment, a method of manufacturing an electrochemical sensing system is provided. The method includes forming a sensor with a first sensing element disposed on a sensor, the first sensing element configured to detect a target gas, disposing a second sensing element on the sensor, the second sensing element configured to detect the target gas, and coupling a protective feature to the second sensing element, the protective feature configured to prevent non-target gases from contacting the second sensing element. The sensor is configured such that if the first sensing element generates a current exceeding a first threshold current value and the second sensing element does not exceed a second threshold current value it is determined that the first sensing element is contaminated and a restoration protocol is performed on the first sensing element.

In addition to one or more of the features described above, or as an alternative, further embodiments may include that the target gas is a low global warming potential gas.

In addition to one or more of the features described above, or as an alternative, further embodiments may include configuring at least one of the first sensing element and the second sensing element to be biased with a voltage.

In addition to one or more of the features described above, or as an alternative, further embodiments may include that both the first sensing element and the second sensing element are configured to be biased with a respective first voltage and a respective second voltage.

In addition to one or more of the features described above, or as an alternative, further embodiments may include configuring the sensor to signal the presence of the target gas.

In addition to one or more of the features described above, or as an alternative, further embodiments may include that the target gas is a first target gas, the method further comprising forming a third sensing element on the sensor, the third sensing element configured to detect a second target gas.

In addition to one or more of the features described above, or as an alternative, further embodiments may include that the first target gas is a low global warming potential gas and the second target gas is carbon monoxide.

In addition to one or more of the features described above, or as an alternative, further embodiments may include configuring the sensor to record a state of health after determining the first sensing element has been contaminated.

In addition to one or more of the features described above, or as an alternative, further embodiments may include that the restoration protocol comprises applying a predetermined biasing voltage to the first sensing element.

According to another embodiment, an electrochemical sensing system is provided. The system includes a first sensing element disposed on a sensor and configured to detect a target gas, a second sensing element disposed on the sensor and configured to detect the target gas, and a protective feature coupled to the second sensing element and configured to prevent non-target gases from contacting the second sensing element. If the first sensing element generates a current exceeding a first threshold value and the second sensing element does not exceed a second threshold value it is determined that the first sensing element is contaminated and a restoration protocol is performed on the first sensing element.

In addition to one or more of the features described above, or as an alternative, further embodiments may include that the target gas is a low global warming potential gas.

In addition to one or more of the features described above, or as an alternative, further embodiments may include that at least one of the first sensing element and the second sensing element is biased with a voltage.

In addition to one or more of the features described above, or as an alternative, further embodiments may include that both the first sensing element and the second sensing element are biased with a respective first voltage and a respective second voltage.

In addition to one or more of the features described above, or as an alternative, further embodiments may include that the target gas is a first target gas, the sensor further comprising a third sensing element configured to detect a second target gas.

In addition to one or more of the features described above, or as an alternative, further embodiments may include that the first target gas is a low global warming potential gas and the second target gas is carbon monoxide.

According to another embodiment, an electrochemical sensing system is provided. The system includes a first sensing element disposed on a sensor and configured to detect a first group of target gases and a group of contaminants, a second sensing element disposed on the sensor and configured to be active to the first group of target gases, a third sensing element disposed on the sensor and configured to be active to at least the first group of target gases, the group of contaminants, a second group of target gases, and a third group of target gases, and a fourth sensing element disposed on the sensor and configured to detect the first of target gases and the third group of target gas. The system further includes a first protective feature coupled to the second sensing element and configured to prevent non-target gases from contacting the second sensing element and a second protective feature coupled to the fourth sensing element and configured to prevent the group of contaminants and the second group of target gases from contacting the fourth sensing element. If the second sensing element and the fourth sensing element each do not generate a current exceeding a respective second threshold value and fourth threshold value and the first sensing element and the third sensing element each generate a current exceeding a respective first threshold value and a third threshold value, it is determined that the third sensing element is contaminated.

In addition to one or more of the features described above, or as an alternative, further embodiments may include that the third sensing element is configured to have a restoration protocol performed thereon In addition to one or more of the features described above, or as an alternative, further embodiments may include that the restoration protocol comprises applying a predetermined voltage to the third sensing element.

In addition to one or more of the features described above, or as an alternative, further embodiments may include that at least one of the third sensing element and the fourth sensing element is biased with a voltage.

In addition to one or more of the features described above, or as an alternative, further embodiments may include that both the third sensing element and the fourth sensing element are biased with a respective first voltage and a respective second voltage.

Technical effects of embodiments of the present disclosure include providing an electrochemical sensor that has efficient state of health monitoring and restoration properties. Further technical effects include applying a predetermined pulse voltage to restore the sensing capability of the electrochemical sensor. Further technical effects include electrochemical gas sensors that are configured to determine when catalyst deactivation has occurred and perform a restoration protocol as needed.

BRIEF DESCRIPTION OF THE DRAWINGS

The subject matter is particularly pointed out and distinctly claimed at the conclusion of the specification. The foregoing and other features, and advantages of the present disclosure are apparent from the following detailed description taken in conjunction with the accompanying drawings in which:

DETAILED DESCRIPTION

As shown and described herein, various features of the disclosure will be presented. Various embodiments may have the same or similar features and thus the same or similar features may be labeled with the same reference numeral, but preceded by a different first number indicating the figure to which the feature is shown. Thus, for example, element "a" that is shown in FIG. X may be labeled "Xa" and a similar feature in FIG. Z may be labeled "Za." Although similar reference numbers may be used in a generic sense, various embodiments will be described and various features may include changes, alterations, modifications, etc. as will be appreciated by those of skill in the art, whether explicitly described or otherwise would be appreciated by those of skill in the art.

Electrochemical ("EC") gas sensors are gas detectors that measure a concentration or determine the presence of a target gas by oxidizing or reducing the target gas at an electrode (e.g., a sensing element) and measuring or detecting a resulting current. The magnitude of the current is governed by how much of the target gas is oxidized at the working electrode portion of the sensor. Electrochemical sensors are usually designed so that the gas supply is limited by diffusion and thus the output from the sensor is linearly proportional to the gas concentration. The linear output of an electrochemical sensor is one of the advantages over other sensor technologies. A linear output allows for precise measurement of low concentrations of a target gas and also allows for simple calibration. Further, electrochemical sensors enable changing of a diffusion barrier or filter to tailor the sensor to be selective to a particular target gas concentration range.

Although not limiting herein, low global warming potential ("LGWP") refrigerants may be one category of gases that are desired to be monitored by electrochemical sensors. LGWP refrigerants may be mildly flammable and thus leak detection may be highly desirable. It may be desirable to employ the same or similar electrochemical sensors that are currently used to sense toxic household gases, such as carbon monoxide, as LGWP refrigerants become more ubiquitous. One challenge of making such a combination EC sensor is that traditional EC sensors are unable to selectively identify gas species, and false alarms may result. Detecting sensor malfunctioning due to reactions of gaseous species is also impossible for traditional EC sensors due to the lack of identification ability. It is known that catalyst (i.e., sensing element) contamination or poisoning by volatile organic compounds ("VOC") in the ambient atmosphere that is around the sensor is a dominant mechanism that may cause failure or faults in the electrochemical sensors. When an EC sensor is deactivated, it may go undetected, leading to failure of the system and the risk of undetected toxic gas or flammable refrigerant leak. A failsafe EC sensor would thus require prevention, detection, and mitigation of catalyst deactivation.

Preventative measures or passive mitigation methods have been used to prevent contamination of a sensing element. For example, activated carbon may be used to target contaminants. This method can be very successful when the sensor is detecting only one gas species, and that species has no adsorption on the adsorbent. However, the use of an adsorbent may interfere with the detection of LGWP refrigerant, due to entrapment of some LGWP refrigerants, resulting in a delayed and/or weaker response of the sensor. Therefore, it may be necessary to have the ability to detect sensor deactivation and, to restore a deactivated sensor when EC sensing is used for refrigerant detection.

Further, LGWP sensors may operate at higher voltages than other types of sensors, i.e., continuously biased, which may cause the LGWP sensors to be more susceptible to a large variety of contaminants that may result in sensor contamination. Sensor state of health determination pertaining to EC sensing is an important aspect of the present disclosure. Although described herein with respect to an LGWP sensor, it will be appreciated by those of skill in the art that the embodiments disclosed herein may be used for any types of sensors, including, but not limited to refrigerant sensors, carbon monoxide sensors, hydrogen sulfide sensors, and/or any other type of electrochemical sensor.

Embodiments described herein enable an electrochemical sensor that has been deactivated by a contaminant, e.g., a VOC, to be recovered by applying a pulse voltage at a sufficiently high level to refresh or restore the sensing element, e.g., restore the catalyst of the sensor. That is, a pulse voltage may be used to convert and remove a contaminant on the surface of the sensing element and to restore the sensor to a fully operational state to detect a target gas.

Figure 1:
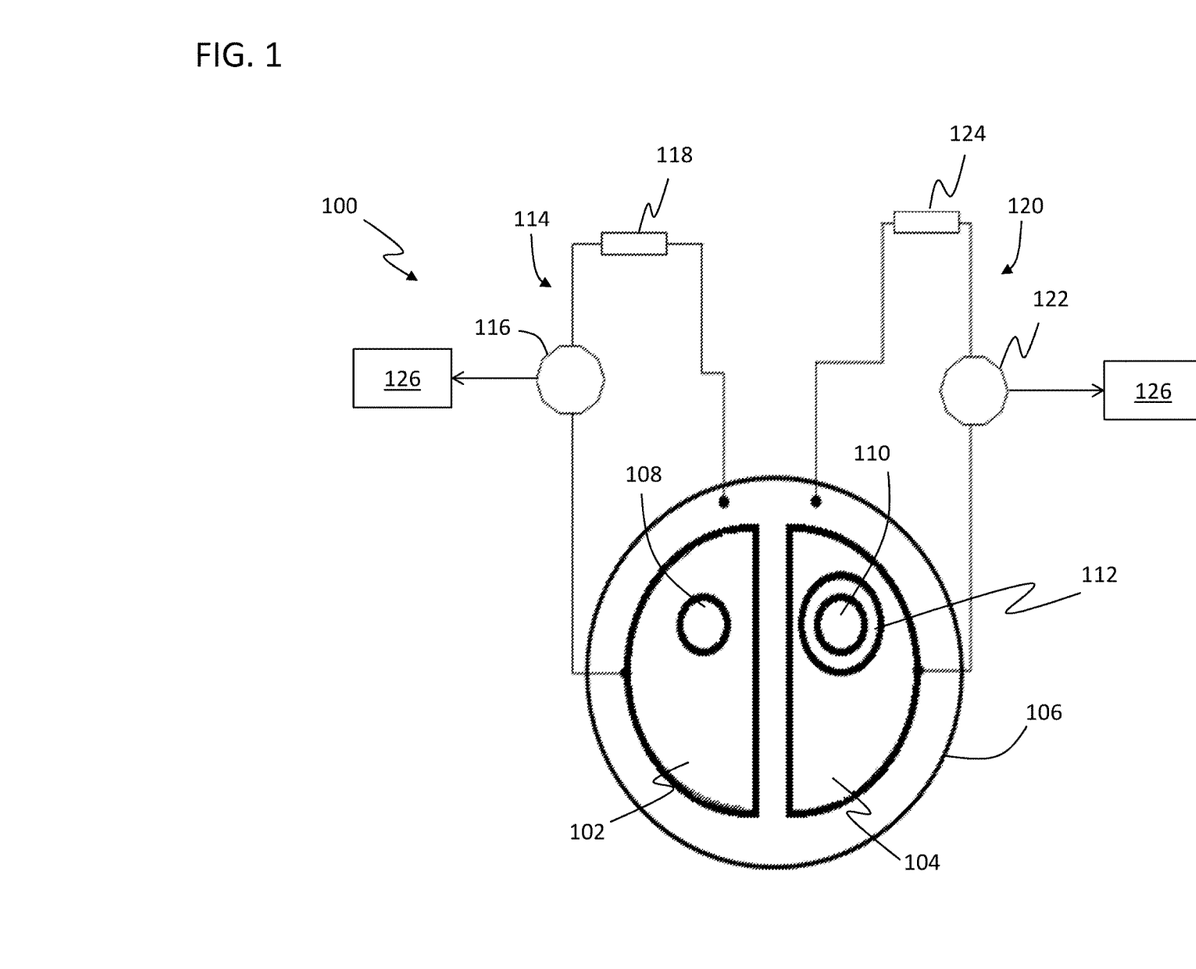
FIG. 1 is a schematic illustration of a sensor in accordance with a non-limiting embodiment of the present disclosure.

FIG. 1 shows a non-limiting embodiment of an electrochemical sensor that may employ embodiments disclosed herein. Sensing system 100 may include two sensing elements: a first sensing element 102 and a second sensing element 104 configured on a sensor 106. In one non-limiting embodiment, the first sensing element 102 and the second sensing element 104 may be identical with respect to composition and may be placed by printing or laminating onto an ion transport medium (separator) such as an ion conduction polymer or liquid electrolyte flooded porous substrate or other sensor structure. A counter electrode (not shown) may be placed on the opposite side of the separator. The first sensing element 102 may be a state of health sensing element and the second sensing element 104 may be configured to detect and/or sense a target gas, i.e., a primary sensing element. The first and second sensing elements 102, 104 may be electrochemical sensing elements as known in the art. For example, the first and second sensing elements 102, 104 may be configured as electrodes and associated electrolytes configured to generate a current when an electrochemically active gas is present.

The first sensing element 102 includes a first aperture 108 configured to allow gases to pass through and interact with the first sensing element 102. The second sensing element 104 includes a second aperture 110 configured to allow only selected or predetermined gases to pass through and interact with the second sensing element 104, such as a target gas. As shown, a protective feature 112 is coupled to the second aperture 110 to filter or absorb gases such that only predetermined or selected gases interact with the second sensing element 104. The protective feature 112 may be configured as an adsorbent, a barrier, a filter, or other device or structure configured to allow some gases to pass therethrough and to prevent other gases from passing therethrough.

In some embodiments, the protective feature 112 may be configured to allow only a target gas to pass therethrough and interact with the second sensing element 104. That is, in some embodiments, the protective feature 112 may be configured or selected to absorb or prevent all other gases from interacting with the second sensing element 104. In some embodiments, the protective feature 112 may adsorb sensor contamination gases, such as VOCs, and prevent the contamination gases from interacting with the second sensing element 104.

The first sensing element 102 is configured with a first sensing circuit 114. The first sensing circuit 114 includes first processing circuitry 116 and a first load 118. When a gas such as the target gas contacts and/or reacts with the first sensing element 102 a current may be generated in the sensing circuit 114 and detected by the processing circuitry 116. The current generated may be proportional to the amount of gas present in the atmosphere. Thus, the first sensing circuit 114 may be used to detect the presence of a target gas. In some embodiments a threshold value may be set such that false alarms or natural concentrations may be avoided. As used herein, a threshold value may be zero or any predetermined value. Depending on the composition of the first sensing element 102, other gases, such as sensor contamination gases, may also interact with the first sensing element 102 and generate current in the first sensing circuit 114.

The second sensing element 104 is similarly configured with a second sensing circuit 120. The second sensing circuit 120 includes second processing circuitry 122 and a second load 124. When a gas such as the target gas is present, it may pass through the protective feature 112 of the second sensing element 104 and interact with the second sensing element 104 to generate a current at the same level as generated in the first sensing element 102. However, as noted, the protective feature 112 may be configured to prevent other gases from interacting with the second sensing element 104. That is, the second sensing element 104 will only have a generated current when the target gas is present, and other gases will not reach and/or react with the second sensing element 104 to generate a current. Again, in some embodiments a threshold value may be set such that false alarms or natural concentrations may be avoided.

Each of the first sensing circuit 114 and the second sensing circuit 120 may be connected to a controller, processor, or other device, e.g., controller 126. The controller 126 may be a processing device having a processor, memory, and other elements and/or components and may be connected to other devices such as alarms, displays, etc. In some non-limiting embodiments, the controller 126 may be configured within the sensor 106 and may be electrically connected to the first sensing circuit 114 and the second sensing circuit 120.

A comparison between response of the first sensing circuit 114 and response of the second sensing circuit 120 may be made, e.g., at the controller 126. If both the first sensing circuit 114 and the second sensing circuit 120 detect a current above the threshold, it may be determined that the target gas is present and appropriate action may be taken, e.g., sound an alarm, activate an emergency system, etc. However, if the first sensing circuit 114 detects a current above the threshold but the second sensing circuit 120 does not, then it may be determined that a contamination gas is present and it may be determined that the first sensing element may be potentially contaminated if extended exposure to that species occurs without reversing the effects. Appropriate action may then be taken. For example, a restoration process or protocol may be initiated to restore the first sensing element 102 after being contaminated. In some embodiments, the controller 126 may be in wireless communication with one or more components of the sensing system 100 and may be physically separate therefrom.

As will be appreciated by those of skill in the art, variations on the sensing system 100 may be made without departing from the scope of the present disclosure. For example, in other embodiments, one or both of the loads 118, 124 may be replaced by biasing voltages that are configured to bias the respective sensing element. Further, in some embodiments, a counter-electrode may be electrically coupled to the sensor and/or one or both of the sensing elements. Further, in some embodiments, the sensing element with the protective feature 112 may be the state of health sensing element and the sensing element without the protective feature may be the primary sensing element, i.e., the reverse of the above described configuration. Furthermore, in some embodiments, the protective feature may be omitted. In some embodiments, one of the sensing elements may be biased and the other sensing element may be unbiased.

Figure 2:
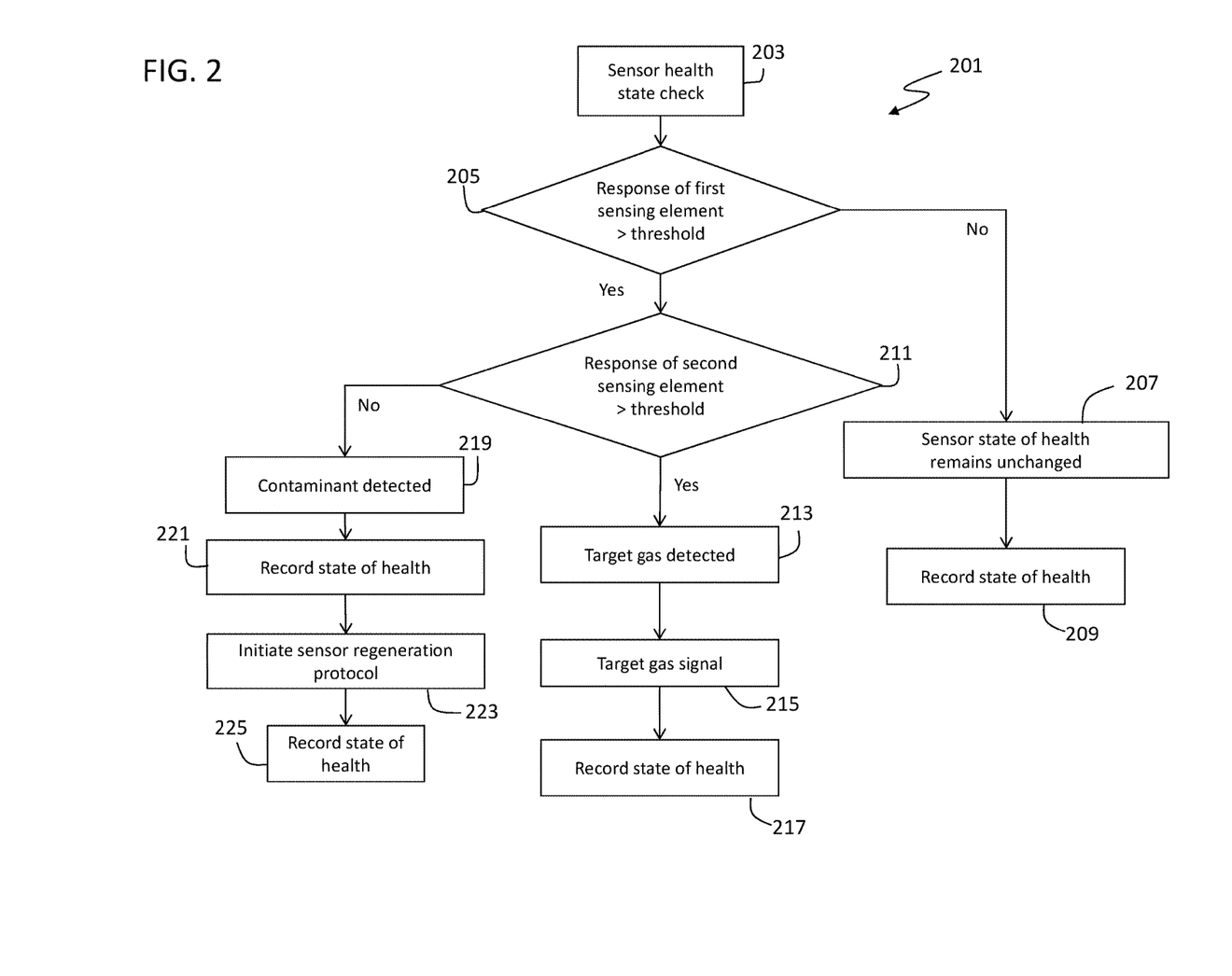
FIG. 2 is a flow chart of a process in accordance with a non-limiting embodiment of the present disclosure.
Figure 4:
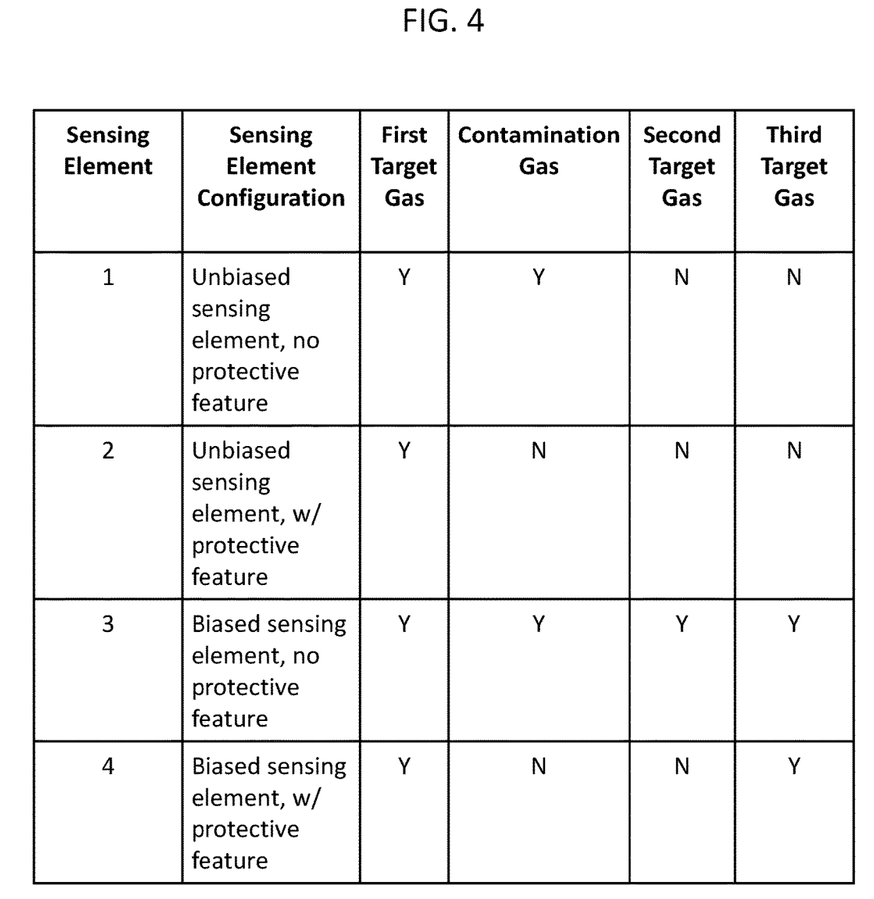
FIG. 4 is a chart of logic for determining the state of health of a sensor configured in one or more non-limiting embodiments of the present disclosure.

Turning now to FIG. 2, a non-limiting embodiment of a process in accordance with the present disclosure is shown. Process 201 is a state of health ("SOH") monitoring and regeneration process for an electrochemical sensor and may be used by a sensor such as sensing system 100 of FIG. 1, where a combination of sensing elements described as sensing elements 1 and 2 in FIG. 4 is included. Process 201 may be performed by appropriate circuitry, components, etc. that are configured to monitor the presence of a target gas in an atmosphere. For example, the process may be performed using one or more sensing systems similar to that shown in FIG. 1 along with appropriate processors, memory, controllers, software, applications, and/or other hardware, components, and/or elements as known in the art.

A sensor health state check may be initiated (step 203). The initiation may be automatic, prompted by software, manually initiated, or otherwise initiated. The health state check may involve comparing responses of sensing elements of the sensing system. As such, it may be determined if a first sensing element, e.g., an unprotected sensing element, generated a current that was greater than a first threshold value (step 205). If the first sensing element did not exceed the first threshold, it may be determined that there has been no change in the state of health of the sensor (step 207). Appropriate circuitry and/or processing equipment may record that no change in health has occurred (step 209), and the process may restart or perform a loop beginning with step 203. Such recording may be made in a memory that may provide for logging or data collection/retention of the state of health of the sensor that is monitored.

If it is determined that the first sensing element has generated a current that exceeded the first threshold (step 205), the logic process may continue to analyze the response characteristics of the second sensing element. It is next determined whether the second sensing element has generated a current that exceeded a second threshold value (step 211). If it is determined that the second threshold is exceeded, it may be determined that a target gas is present (step 213). That is, because the first sensing element and the second sensing element are the same and the second sensing element includes a protective feature that only permits the target gas to interact with the second sensing element, it may be positively determined that the target gas is present. Accordingly, an appropriate action, such as signaling the presence of the target gas (step 215), may be performed. The signal may include visual alerts, audible alerts, digital notifications, activation of emergency systems, etc., as known in the art. Additionally, when the target gas is detected the event may be logged or recorded (step 217)

However, if it determined that the second sensing element has not exceeded the second threshold (step 211) but the first sensing element has exceeded the first threshold, it may be determined that a contamination gas is present (step 219). Contaminants may include gases that may poison or damage the ability of the sensing system to detect the target gas. When it is determined that a contamination gas is present, the state of the health of the sensing system may be recorded or logged, i.e., it may be recorded that a contaminant was present (step 221). If a contaminant is determined to be present (step 219) and the first sensing element is thus contaminated, the first sensing element may be required to be regenerated or restored such that it may return to a healthy state. Thus, a restoration protocol or process may be performed (step 223). The restoration protocol may involve subjecting the first sensing element to a biasing voltage sufficient to burn off or otherwise remove the contaminant from the first sensing element. Subsequently, the restoration may be recorded (step 225).

In some non-limiting embodiments, steps 203, 207, and 209 may be omitted, and the process may begin at step 205 when the first sensing element exceeds the first threshold. That is, when the first sensing element exceeds the first threshold, the process 201 is initiated such that a comparison between the first sensing element and the second sensing element is made.

Figure 3:
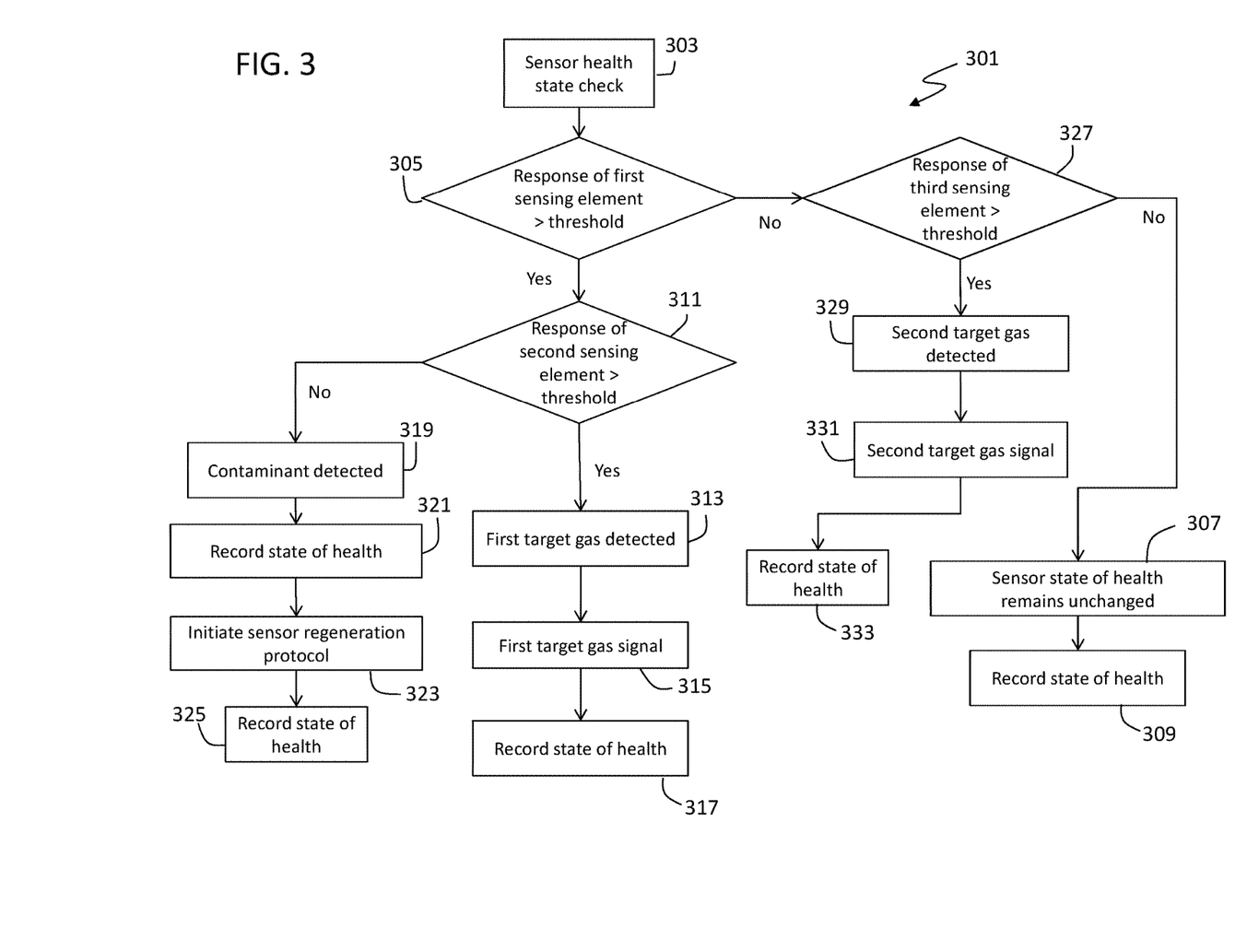
FIG. 3 is a flow chart of a process in accordance with an alternative non-limiting embodiment of the present disclosure.

Turning now to FIG. 3, an alternative, non-limiting embodiment of a process in accordance with the present disclosure is shown. The process 301 shown in FIG. 3 is substantially similar to that shown in FIG. 2, but a third sensing element is configured as part of the sensing system. Such configuration may enable the detection of more than one target gas, while allowing for determining when a restoration or regeneration of one or more sensing elements may be required.

A non-limiting example of a sensing system that may be used to perform the process 301 may be one configured with an open, unbiased first sensing element (i.e., no protective feature (non-filtration, non-adsorption) and no biasing voltage), a protected, unbiased second sensing element (i.e., protective feature and unbiased electrode), and a biased, open third sensing element (i.e., no protective feature and biasing voltage). Each of the sensing elements may have identical or different catalyst composition, but configured differently with respect to the presence of a protective feature and/or biasing of the sensing element, i.e., the application of a voltage to the sensing element.

In process 301, a sensor health state check may be initiated (step 303) similar to that described above. The health state check may involve comparing responses of the sensing elements of the sensing system. As such, it may be determined if the first sensing element generated a current that was greater than a first threshold value (step 305).

If it is determined that the first sensing element has generated a current that exceeded the first threshold (step 305), the process may continue to the second sensing element. It then is determined whether the second sensing element has generated a current that exceeded a second threshold value (step 311). If it is determined that the second threshold is exceeded, it may be determined that a first target gas is present (step 313). That is, because the first sensing element and the second sensing element are the same and the second sensing element includes a protective feature that only permits the first target gas to interact with the second sensing element, it may be positively determined that the first target gas is present. Accordingly, an appropriate action, such as signaling the presence of the first target gas (step 315), may be performed. The signal may include visual alerts, audible alerts, digital notifications, emergency actions, etc., as known in the art. Additionally, when the first target gas is detected the event may be logged or recorded (step 317).

However, if it determined that the second sensing element has not exceeded the second threshold (step 311), and the first sensing element has exceeded the first threshold, it may be determined that a contamination gas is present (step 319). Contaminants may include gases that may poison or damage the ability of the sensing system to detect the target gases. The state of the health of the sensing system may be recorded or logged, i.e., it may be recorded that a contaminant is present (step 321). If a contaminant is determined to be present (step 319) the first sensing element may be required to be regenerated or restored such that it may maintain a healthy state. Thus, a restoration protocol or process may be performed (step 323). The restoration process may involve subjecting the first sensing element to a biasing voltage sufficient to convert or otherwise remove the contaminant from the first sensing element.

Still referring to process 301, if the first sensing element did not exceed the first threshold (step 305), the process 301 may continue to the third sensing element. A determination is made whether the third sensing element has generated a current that is greater than a third threshold (step 327). If the third sensing element is determined to have exceeded the third threshold, it may be determined that a second target gas is present (step 329). Accordingly, an appropriate action, such as signaling the presence of the second target gas (step 331), may be performed. The signal may include visual alerts, audible alerts, digital notifications, emergency actions, etc., as known in the art. When the second target gas is detected the event may be logged or recorded (step 333).

If there is no response in the first sensing element and no response in the third sensing element, i.e., no induced currents, it may be determined that there has been no change in the state of health of the sensing system (step 307). Appropriate circuitry and/or processing equipment may record that no change in health has occurred (step 309). Such recording may be made in a memory that may provide for logging of the state of health of the sensing system that is monitored.

Turning now to FIG. 4, a table providing one non-limiting example of a four-sensing-element sensing system is shown. The first column provides the sensing element number, the second column provides the sensing element configuration (e.g., biased, protective feature, etc.), and columns three through six provide the gas and response of the associated sensing element where "Y" represents positive response and "N" represents no response from the respective sensing/SOH elements. The above described processes, and/or variations thereof, may be performed with a sensing system or configured with the elements shown in FIG. 4. Further, those of skill in the art will appreciate that more or fewer sensing elements and sensing element configurations may be employed without departing from the scope of the present disclosure. Moreover, it will be appreciated by those of skill in the art that the unprotected or "open" sensing elements may require restoration as described above.

The first sensing element may be an unbiased sensing element with no protection, i.e., no protective feature. The second sensing element may be an unbiased sensing element with a protective feature. The third sensing element may be a biased sensing element with no protection, i.e., no protective feature. The fourth sensing element may be a biased sensing element with a protective feature. Thus, a sensing system configured with the four above sensing elements may be able to detect the presence of multiple target gases and/or determine when various sensing elements of the sensor may require to be regenerated, i.e., when contamination gases are present.

For example, when all four sensing elements generate a current above a threshold set for each sensing element, a first target gas may be determined to be present and appropriate action may be taken (e.g., perform a signal or other alert regarding the first target gas). If, however, only the first and the third sensing elements generate a current above the respective thresholds and the second and fourth sensing elements do not exceed the respective thresholds, then it may be determined that a contamination gas is present and appropriate action may be taken, e.g., a restoration protocol may be carried out. Similar sensing element current generations or lack thereof may be appreciated from FIG. 4. Throughout any and all iterations, the system may be configured to log which gases are present and/or what action is taken and when. Thus, a historical log or record may be maintained by or for the sensing system.

As will be appreciated by those of skill in the art, various combinations or changes, substitutions, and/or additions may be made with respect to the sensing element configurations or numbers thereof without departing from the scope of the present disclosure. For example, the chart shown in FIG. 4 may be employed to configure a sensing system having any desired combination of sensing elements.

Advantageously, embodiments described herein provide an electrochemical gas sensor or sensing system configured to monitor the state of health of the sensor or sensing system and determine when a restoration process should be performed on one or more sensing elements of the sensor or sensing system. Further, advantageously, embodiments described herein enable multiple-sensing-element sensors that may be configured to detect multiple types of gases, ranging from multiple target gases to contaminating gases, and further enable determination of poisoning of one or more of the sensing elements. Additionally, restorative processes may be performed based on the various sensing elements in view of the processes disclosed herein.

Further, advantageously, false alarms regarding a target gas may be eliminated. For example, if both a first and second sensing element are configured to detect a target gas, but the second sensing element has a protective feature as described herein, it may be possible to determine when the first sensing element has been contaminated with a gas or substance that may induce a current in the sensing element and thus potentially trigger a signal or alarm. However, because the second sensing element includes the protective feature, and thus not have an induced current, it may be deduced that the activation of the first sensing element was due to a contaminant that is not the target gas, and thus a false alarm may be avoided.

Moreover, advantageously, embodiments disclosed herein enable a sensor to be configured to monitor for target gases for substantially the entire life of the sensor. That is, a regeneration protocol, which may prevent detection of a target gas, may only be performed when needed, and thus at all other times, the sensor may be able to detect a target gas. In other words, embodiments disclosed herein reduce the amount of downtime of a sensor due to restoration protocols performed on the sensor.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions, combinations, sub-combinations, or equivalent arrangements not heretofore described, but which are commensurate with the spirit and scope of the present disclosure. Additionally, while various embodiments of the present disclosure have been described, it is to be understood that aspects of the present disclosure may include only some of the described embodiments.

For example, although described and shown herein with respect to a single sensor configuration, those of skill in the art will appreciate that various other configurations of sensor(s) and/or sensing systems may be employed without departing from the scope of the present disclosure. For example, sensors having two or more sensing elements, however configured, may employ embodiments disclosed herein. Further, sensors may have sensing elements with or without protective features, and may be biased or unbiased, and still employ embodiments disclosed herein. Moreover, although described with respect to LGWP gases, those of skill in the art will appreciate that any target gas may be configured to be sensed and/or any contaminating gas may be configured to be monitored for by systems and processes disclosed herein.

Accordingly, the present disclosure is not to be seen as limited by the foregoing description, but is only limited by the scope of the appended claims.

What is claimed is:

1. A method of manufacturing an electrochemical sensing system, the method comprising:
    forming a sensor with a first sensing element disposed on a sensor, the first sensing element configured to detect a target gas;
    disposing a second sensing element on the sensor, the second sensing element configured to detect the target gas; and
    coupling a protective feature to the second sensing element, the protective feature configured to prevent non-target gases from contacting the second sensing element,
    the sensor configured such that if the first sensing element generates a current exceeding a first threshold current value and the second sensing element does not exceed a second threshold current value it is determined that the first sensing element is contaminated and a restoration protocol is performed on the first sensing element.

2. The method of claim 1, wherein the target gas is a low global warming potential gas.

3. The method of claim 1, further comprising configuring at least one of the first sensing element and the second sensing element to be biased with a voltage.

4. The method of claim 3, wherein both the first sensing element and the second sensing element are configured to be biased with a respective first voltage and a respective second voltage.

5. The method of claim 1, further comprising configuring the sensor to signal the presence of the target gas.

6. The method of claim 1, wherein the target gas is a first target gas, the method further comprising forming a third sensing element on the sensor, the third sensing element configured to detect a second target gas.

7. The method of claim 5, wherein the first target gas is a low global warming potential gas and the second target gas is carbon monoxide.

8. The method of claim 1, further comprising configuring the sensor to record a state of health after determining the first sensing element has been contaminated.

9. The method of claim 1, wherein the restoration protocol comprises applying a predetermined biasing voltage to the first sensing element.

10. An electrochemical sensing system comprising:
    a first sensing element disposed on a sensor and configured to detect a target gas;
    a second sensing element disposed on the sensor and configured to detect the target gas; and
    a protective feature coupled to the second sensing element and configured to prevent non-target gases from contacting the second sensing element,
    the sensor configured such that if the first sensing element generates a current exceeding a first threshold current value and the second sensing element does not exceed a second threshold current value it is determined that the first sensing element is contaminated and a restoration protocol is performed on the first sensing element.

11. The electrochemical sensing system of claim 10, wherein the target gas is a low global warming potential gas.

12. The electrochemical sensing system of claim 10, wherein at least one of the first sensing element and the second sensing element is biased with a voltage.

13. The electrochemical sensing system of claim 12, wherein both the first sensing element and the second sensing element are biased with a respective first voltage and a respective second voltage.

14. The electrochemical sensing system of claim 10, wherein the target gas is a first target gas, the sensor further comprising a third sensing element configured to detect a second target gas.

15. The electrochemical sensing system of claim 14, wherein the first target gas is a low global warming potential gas and the second target gas is carbon monoxide.

16. An electrochemical sensing system comprising:
a first sensing element disposed on a sensor and configured to detect a first group of target gases and a group of contaminants;
a second sensing element disposed on the sensor and configured to be active to the first group of target gases;
a third sensing element disposed on the sensor and configured to be active to at least the first group of target gases, the group of contaminants, a second group of target gases, and a third group of target gases;
a fourth sensing element disposed on the sensor and configured to detect the first of target gases and the third group of target gas;
a first protective feature coupled to the second sensing element and configured to prevent non-target gases from contacting the second sensing element; and
a second protective feature coupled to the fourth sensing element and configured to prevent the group of contaminants and the second group of target gases from contacting the fourth sensing element;
the sensor configured such that if the second sensing element and the fourth sensing element each do not generate a current exceeding a respective second threshold value and fourth threshold value and the first sensing element and the third sensing element each generate a current exceeding a respective first threshold value and a third threshold value, it is determined that the third sensing element is contaminated and a restoration protocol is performed on the third sensing element.

17. The electrochemical sensing system of claim 16, wherein the restoration protocol comprises applying a predetermined voltage to the third sensing element.

18. The electrochemical sensing system of claim 16, wherein at least one of the third sensing element and the fourth sensing element is biased with a voltage.

19. The electrochemical sensing system of claim 18, wherein both the third sensing element and the fourth sensing element are biased with a respective first voltage and second voltage.

* * * * *